US00PP35287P2

(12) United States Plant Patent
Hansen

(10) Patent No.: US PP35,287 P2
(45) Date of Patent: Jul. 25, 2023

(54) ***MONARDA* PLANT NAMED 'PINK CHENILLE'**

(50) Latin Name: ***Monarda* hybrid**
Varietal Denomination: Pink Chenille

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 17/803,790

(22) Filed: Nov. 22, 2022

(51) Int. Cl.
*A01H 5/02* (2018.01)
*A01H 6/50* (2018.01)

(52) U.S. Cl.
USPC ..... Plt./455

(58) Field of Classification Search
USPC ..... Plt./263.1, 455
See application file for complete search history.

*Primary Examiner* — Karen M Redden

(57) ABSTRACT

The new and distinct cultivar of ornamental cultivar of Bee Balm plant *Monarda* named 'Pink Chenille' has medium-height, dense, branching stems, dark green glossy foliage with strong resistance to powdery mildew, numerous large flower heads of fluorescent-pink-colored flowers creating excellent flower coverage. Flower heads are subtended by wine-colored bracts. The new plant is attractive and useful in the garden landscape as a specimen, en masse, or as a container plant.

1 Drawing Sheet

Botanical classification: *Monarda* hybrid.
Variety denomination: 'Pink Chenille'.

STATEMENT REGARDING PRIOR DISCLOSURES UNDER 37 CFR 1.77(b)(6)

The first non-enabling information of the newly claimed plant was made on Dec. 1, 2021, in the form of photographs and a brief description on websites operated by Walters Gardens, Inc. and Proven Winners®, followed on Jun. 8, 2022, by a photograph and brief description in the "Walters Gardens 2022-2023 Catalog." Walters Gardens, Inc. and Proven Winners® obtained the plant and all information relating thereto, from the inventor. The first sales of the new plant were on Jul. 11, 2022, by Walters Gardens, Inc., which obtained the new plant and all information about the new plant from the inventor. No plants of *Monarda* 'Pink Chenille' have been sold, in this country or anywhere in the world, nor has any disclosure of the new plant been made more than one year prior to the filing date of this application, and such sale or disclosure within one year was either derived directly or indirectly from the inventor and would therefore be a 35 U.S.C. § 102b exception.

BACKGROUND OF THE INVENTION

The present invention relates to the new and distinct cultivar of Bee Balm plant, botanically known as *Monarda* 'Pink Chenille', and hereinafter also referred to solely as the cultivar 'Pink Chenille' or the "new plant". The new plant was selected from a self-pollination on Jun. 17, 2015, from an unreleased, proprietary hybrid known only by the hybridizer code 14-17-1 in a designated hybridizing plot of a wholesale perennial nursery in Zeeland, Mich., USA. The new plant was a single seedling selection originally made in the summer of 2017 from the seeds that were sown in the fall of 2015 and the plant was assigned the breeder code of 15-53-4. Further selection was completed in the research facility of a wholesale perennial nursery in Zeeland, Mich. in the summer of 2019.

The new plant has been asexually propagated first by division in the summer of 2017 followed by shoot tip cuttings in 2019 at the same nursery in the greenhouses in Zeeland, Mich., and the subsequent asexually propagated plants have been found to be stable, true to type and identical to the original selection.

BRIEF SUMMARY OF THE PLANT

*Monarda* 'Pink Chenille' is unique from its parents and all other Bee Balm plants known to the inventors. The nearest comparison varieties are: 'Pardon My Rose' U.S. Plant Pat. No. 34,434, 'Leading Lady Pink' U.S. Plant Pat. No. 34,205, 'Electric Neon Pink' U.S. Plant Pat. No. 30,347, 'Berry Taffy' U.S. Plant Pat. No. 34,715, 'Petite Delight' U.S. Plant Pat. No. 10,784, and 'AChall' U.S. Plant Pat. No. 19,582.

'Pardon My Rose' has a shorter habit with flowers that are slightly different pink flowers with lighter pink spots. 'Leading Lady Pink' has a more compact shorter habit with flowers that are bright-pink with lighter spots in the lower petal. 'Electric Neon Pink' has a similar habit with flowers that are a darker neon-pink. 'Berry Taffy' has a more compact shorter habit with flowers that are hot raspberry-pink without darker spotting on the lower lip.

'Petite Delight' is significantly shorter than the new plant and the flowers are smaller and slightly different hue of purplish-red without darker spots. 'AChall' has a slightly shorter habit than the new plant, and has flowers that are slightly different hue of purplish-red without the darker spots. Both 'Petite Delight' and 'AChall' showed more sensitivity to powdery mildew.

The parent plant has a taller and more open habit and the flower color is a lighter pink.

The following are traits of *Monarda* hybrid 'Pink Chenille' that in combination distinguish it from all other Bee Balm known to the inventor:

1. Medium-height, winter-hardy, dense, vigorous, highly-branching, clumping habit;
2. Dark-green glossy leaves that are strongly resistant to powdery mildew;
3. Large flower heads of fluorescent-pink-colored flowers for a long period in summer with excellent flower coverage;
4. Flower heads are subtended by wine-colored bracts.

BRIEF DESCRIPTION OF THE DRAWINGS

The photographs of the new plant demonstrate the unique traits of 'Pink Chenille' and the overall appearance of a three-year-old plant in a full-sun, outdoor, research facility of a wholesale perennial nursery in Zeeland, Mich. The colors are as accurate as reasonably possible with color reproductions. Variations in the ambient light spectrum, source, and direction may cause the appearance of minor variations in color.

DETAILED BOTANICAL DESCRIPTION

Figure 1:
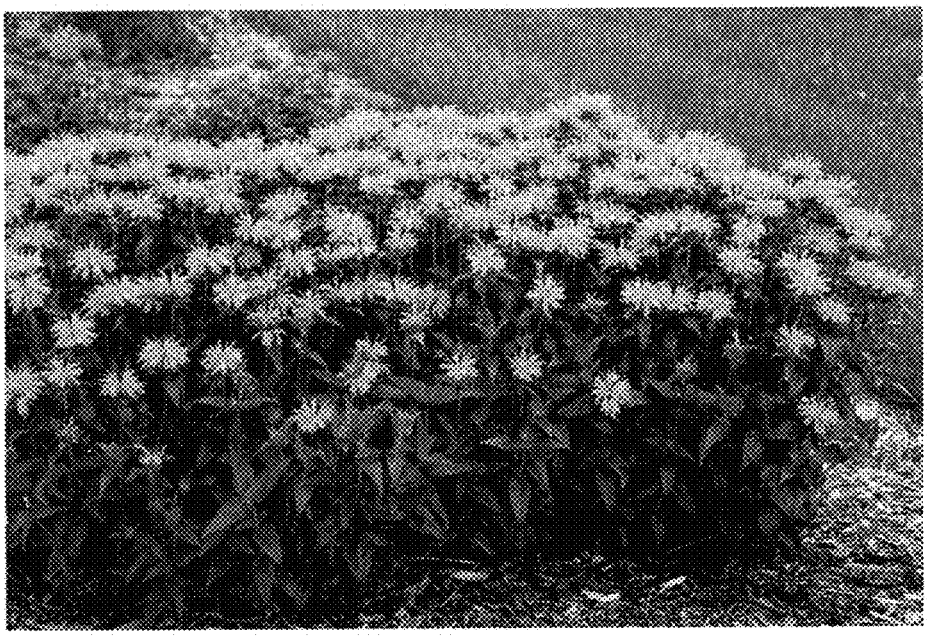
FIG. 1 shows the new plant in flower in the research facility.
Figure 2:
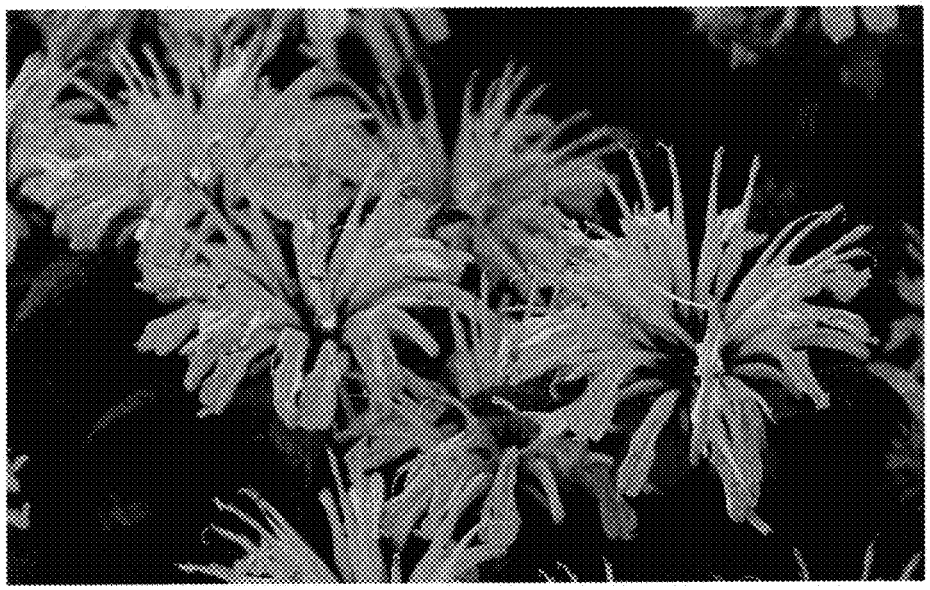
FIG. 2 shows a close-up of the flowers.

The following descriptions and color references are based on the 2015 edition of The Royal Horticultural Society Colour Chart except where common dictionary terms are used. *Monarda* hybrid 'Pink Chenille' has not been observed under all possible environments. The phenotype may vary slightly with different growing environments such as temperature, light, fertility, soil pH, moisture, and maturity levels, but without any change in the genotype. The following observations and size descriptions are based on two-year-old plants in a display garden at a nursery in Zeeland, Mich. with supplemental fertilizer and water as needed but without plant growth regulators or pinching.

Botanical classification: *Monarda* hybrid including the species *didyma, fistulosa, bradburiana*, and *pringlei;*

Parentage: The parent plant is the proprietary hybrid known only as 14-17-1;

Plant habit: Winter-hardy herbaceous perennial, compact, producing several stems spreading by short rhizomes; to 55 cm tall at flowering and 47 cm wide; flowering beginning early-summer in Michigan and continuing for about 4 weeks;

Propagation: Stem cuttings;

Time to produce finished crop in 3.8-liter pots: About 8 to 10 weeks; vigorous rate of growth;

Root: Fine, fibrous, and freely-branching; color creamy white to tan depending on soil type;

Leaves: Simple; lanceolate; opposite; serrated; finely and sparsely puberulent above and below; lustrous above, matte below; acute apex, rounded to cordate base; to about 66 mm long and about 33 mm wide, decreasing distally, average about 60 mm long and 30 mm wide;

Leaf color: Young expanding leaves between RHS 143A and RHS 144A on adaxial surface and on abaxial surface nearest RHS 144A; mature adaxial leaves between RHS 139A and RHS NN137A and abaxial leaves between RHS 137B and RHS 137A;

Foliage fragrance: Pleasant lemony;

Veins: Pinnate; pubescent below with minute puberulent above, slightly sunken above and costate below;

Vein color: Mature adaxial proximal midrib and proximal and central primary veins nearest RHS 195B, distal midrib and veins nearest RHS 138D; mature abaxial midrib nearest RHS 145C, abaxial veins nearest RHS 146C; emerging adaxial midrib and primary veins nearest RHS 146C, emerging abaxial surfaces nearest RHS 147C;

Petiole: Glabrescent to puberulent; slightly concavo-convex; to about 4 mm long and 2.5 mm across, decreasing distally;

Petiole color: Adaxial nearest RHS 148C without anthocyanin, abaxial center nearest RHS 145C, and margin nearest RHS 137A;

Stems: Quadrangular, puberulent, to about 52 cm long and 3 mm across at base;

Stem color: Basal portion between RHS 146C and RHS 146D, distal portion between RHS 145A and RHS 146D without significant anthocyanin;

Branches: In middle and distal nodes; quadrangular; puberulent; typically, eight to twelve per main stem at initial flowering; about 2 mm across at base and to about 23 cm long;

Branch color: Proximally between RHS 145A and RHS 146D;

Nodes: About 12 to 16 per stem; pubescent;

Node color: Nearest RHS 146D with a thin horizontal band of nearest RHS N187A;

Flowers: Single, labiate, actinomorphic flowers arranged in terminal verticillate head about 80 mm across and 40 mm tall, opening from the center and progressing outwardly and downwardly; individual flowers to about 40 mm long to exserted pistil; corolla to about 36 mm long, 14 mm tall and 5 mm across; numerous, about 120 to 250 flowers per head; flower altitude upright in the center of the head to outwardly toward the perimeter, slightly arcuate distally; self-cleaning;

Flower lasting: Individual flowers persisting about 5 days in Michigan, head remains effective for 2 to 3 weeks;

Flower period: Usually late June to late July; about four weeks;

Flower fragrance: None observed;

Buds one to two days prior to opening: Narrowly clavate; tubular; rounded apex; arcuate slightly downward in distal half; about 27 mm long, about 3 mm across in the middle, and about 5 mm tall;

Bud color one to two days prior to opening: Between RHS N66B and RHS N66C;

Petals: Bilabiate; arcuate downward; fused in proximal 21 mm, split in two in about the distal 15 mm; puberulent abaxial and glabrous adaxial except pubescent in center 3 to 5 mm of lower lip;

Upper labium: Folded into a hood about 14 mm long from fusion and 2.5 mm across and 3.0 mm tall just distal fusion;

Lower labium: About 15 mm long from fusion, comprising three lobes including two side lobes about 1 mm long and 2 mm across having rounded apex entire margin, and center lobe to about 3 mm long and 1 mm wide, folded back over lip, with emarginate apex split in the distal 0.5 mm and entire margin;

Petal color: Basal adaxial and abaxial basal 6 mm of corolla tube nearest RHS N155C; adaxial upper labium distal portion nearest RHS N66C, abaxial distal free portion between RHS 61B and RHS 61C; lower labium adaxial between RHS 63B and RHS 61C with spots of between RHS 61B and RHS 61A, abaxial distal free portion between RHS 61B and RHS 61C; adaxial and abaxial lobes RHS 63B and RHS 61C without spots; distal two-thirds of corolla tube adaxial nearest RHS 61D, and abaxial nearest RHS 61C;

Floral bracts: Two sets, between 5 and 8 in each set subtending flower head; proximal set, with acuminate to narrowly acute apex, sessile rounded base, and serrate margin; to about 45 mm long and 22 mm wide; distal set lanceolate to linear with narrowly acute apex, sessile acuminate base, and ciliolate margin; to about 20 mm long and 5 mm wide near base;

Floral bract color: Proximal set adaxial variable, nearest RHS NN137A with basal deltoid region about one-third the length nearest RHS 145C, distally variably blushed to solid RHS N186C, abaxial between RHS 146A and RHS 138A; distal set adaxial portion strongly blushed to solid nearest RHS N186C proximal portion variable between RHS 147D and RHS 148B, abaxial between RHS 147B and RHS 147C blushed with variable amount of anthocyanin distally nearest RHS N186C;

Androecium: Two;

*Filaments*.—Two, to about 36 mm long by 0.3 mm diameter; adnate to inner corolla tube in proximal 15 mm; color nearest RHS N66D, distally lighter than RHS N66D.

*Anther*.—Two; connate; oblong-elliptic, dorsifixed, longitudinal; 3 mm by 1 mm; color nearest RHS 71B.

*Pollen*.—Abundant, elliptic to globose, less than 0.1 mm; color between RHS 10A and RHS 10B.

Gynoecium: One per flower; about 38 mm long at maturity, exserted;

*Style*.—About 35 mm by 0.3 mm; color nearest RHS 69D.

*Stigma*.—Split in two in the distal 2 mm, 0.2 mm in diameter; color nearest RHS NN74B.

*Ovary*.—1.0 mm by 0.75 mm; color between RHS 143D and RHS 144B.

*Calyx*.—Tubular to campanulate, consisting of five fused sepals; about 9 mm long and 3 mm diameter at apex with calyx tube base about 0.7 mm diameter.

Sepals: Five; apiculate apex; margin micro-serrulate; basal 7 mm fused forming corolla tube; about 9 mm long and 1 mm across at fusion; glabrous adaxial and abaxial;

Sepal color: Adaxial and abaxial distal free portion nearest RHS N186B; adaxial proximally nearest RHS 138C, abaxial basal portion nearest RHS 195D, central portion nearest RHS 147C, and distal portion nearest RHS 187B with darker veins distally of nearest RHS 187A;

Pedicel: Short, cylindrical; glabrous; about 1 mm long and 0.5 mm diameter;

Pedicel color: Nearest RHS 147C;

Peduncle: Pubescent; stiff; strong; erect; quadrangular to about 2.5 mm across and about 70 mm long just above last leaves;

Peduncle color: Nearest RHS 146C;

Fruit: Single nutlet, elliptical, about 1.0 mm long and 0.7 mm wide; color nearest RHS 202A;

Hardiness: The new plant grows best with plenty of moisture and adequate drainage; hardy to at least from USDA zone 4 through 8;

Disease and pest resistance: Demonstrated strong powdery mildew resistance (*Sphaerotheca pannosa* var. *rosa*) in side-by-side comparison better than that of 'Petite Delight' and 'AChall'.

I claim:

1. A new and distinct cultivar of ornamental Bee Balm *Monarda* plant named 'Pink Chenille', as herein described and illustrated.

* * * * *